United States Patent [19]

Selwitz et al.

[11] 4,369,123

[45] Jan. 18, 1983

[54] STABLE EMULSIONS OF SUBSTANTIALLY PURE ALKENYLSUCCINIC ACID AND THEIR PREPARATION

[75] Inventors: Charles M. Selwitz, Monroeville; Johann G. Schulz, Pittsburgh, both of Pa.

[73] Assignee: Gulf Research & Development Company, Pittsburgh, Pa.

[21] Appl. No.: 161,113

[22] Filed: Jun. 19, 1980

[51] Int. Cl.$^3$ .............................................. B01J 13/00

[52] U.S. Cl. .................................... 252/312; 562/595; 252/314

[58] Field of Search ......................... 252/312; 562/595

[56] References Cited

U.S. PATENT DOCUMENTS

| | | | |
|---|---|---|---|
| 2,283,214 | 5/1942 | Kyrides | 562/595 X |
| 4,158,664 | 6/1979 | Selwitz et al. | 562/595 X |

*Primary Examiner*—Bernard Helfin

*Attorney, Agent, or Firm*—Deane E. Keith; Forrest D. Stine; Joseph J. Carducci

[57] ABSTRACT

A stable, isotropic emulsion of substantially pure alkenylsuccinic acid-in-water is prepared without using an emulsifying agent. The emulsion is prepared by heating an admixture of substantially pure alkenylsuccinic acid and water at a temperature of at least about 63° C., cooling the heated mixture to below about 40° C. and subjecting the cooled mixture to brisk agitation at a temperature below about 50° C. to form a stable emulsion. The average particle diameter of the alkenylsuccinic acid particles is less than about 30 microns.

15 Claims, No Drawings

STABLE EMULSIONS OF SUBSTANTIALLY PURE ALKENYLSUCCINIC ACID AND THEIR PREPARATION

CROSS-REFERENCE TO RELATED APPLICATION

Reference is made to the following U.S. application filed on even date:

U.S. patent application Ser. No. 161,188 filed June 19, 1980 to Charles M. Selwitz and J. G. Schulz entitled "Alkenylsuccinic Acid Emulsions And Their Preparation", which application is hereby incorporated by reference.

FIELD OF THE INVENTION

The present invention relates to stable, aqueous emulsions of alkenylsuccinic acids and to the process for producing such stable emulsions. More particularly, this invention relates to stable, aqueous emulsions comprising alkenylsuccinic acids wherein such emulsions can be prepared without using emulsifying agents by a relatively simple procedure.

DESCRIPTION OF THE PRIOR ART

Alkenylsuccinic acids are useful in the production of cosmetics, for example, as components of hand lotions, in printing inks, and in floor polishes, for example, by incorporation into paraffin waxes to increase the hardness thereof. The use of the alkenylsuccinic acids in such products requires that it be emulsified in water for incorporation therein. However, conventional emulsifying agents, such as nitrogenous compounds including various amines, may cause skin irritations when the emulsion comes in contact with the skin.

U.S. Pat. No. 4,158,664 to C. M. Selwitz and H. I. Thayer discloses a process for improving the color of normally dark alkenylsuccinic anhydrides which involves treating such materials with water in order to produce a solid, light amber product having more commercial appeal. The use of the resulting product in an aqueous emulsion would be expected to require the use of conventional emulsifying agents because of its waxy nature.

SUMMARY OF THE INVENTION

It has now been found that a stable, isotropic emulsion of alkenylsuccinic acids in water can be produced by a process which comprises heating an admixture of substantially pure alkenylsuccinic acid and water at a temperature above about 63° C., cooling the resulting mixture to a temperature below about 40° C., and then subjecting the admixture to brisk agitation while maintaining the temperature thereof below about 50° C., thereby forming a stable emulsion.

Surprisingly, it was found that despite the waxy nature of the alkenylsuccinic acid, it can be formed into a stable emulsion in the absence of conventional emusifying agents, i.e., materials possessing both hydrophilic and lipophilic moieties, and which aid in the formation of an emulsion. Thus, the alkenylsuccinic acid-in-water emulsions of the present invention experience no appreciable separation of water and alkenylsuccinic acid within a period of at least 10 days, despite the fact that such emulsion contains only substantially pure alkenylsuccinic acid and water.

DESCRIPTION OF THE PREFERRED EMBODIMENTS

The stable emulsions of the present invention are formed by heating an admixture of a substantially pure alkenylsuccinic acid and water to a temperature of at least about 63° C., cooling the resulting mixture to a temperature below about 40° C. and then subjecting the admixture to brisk agitation while maintaining the temperature below about 50° C. to form a stable emulsion of the alkenylsuccinic acid in water.

Any suitable alkenylsuccinic acid can be emulsified according to the present invention. One such alkenylsuccinic material has the following structural formula:

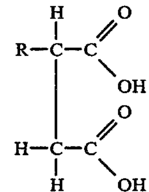

wherein R is an alkenyl group, straight or branched chain, having from 26 to 100 carbon atoms, preferably from 30 to 60 carbon atoms.

Suitable alkenylsuccinic acids and their corresponding anhydrides can be prepared in any conventional manner known in the art, including that described in U.S. Pat. No. 4,158,664 to Selwitz, et al, the disclosure of which is hereby incorporated by reference.

Thus, one procedure for preparing such compounds involves, for example, reacting, with stirring, a mixture of a straight or branched olefin and maleic anhydride at a molar ratio of olefin to maleic anhydride of about 0.5:1 to about 2:1, preferably about 0.8:1 to about 1.25:1 at a temperature of about 140° to about 250° C., preferably about 180° to about 220° C., and a pressure of about 0.1 to about 1000 pounds per square inch gauge (about 0.69 to about 6895 kPa), preferably about 10 to about 20 pounds per square inch gauge (about 68.95 to about 137.9 kPa), for about three to about 60 hours, preferably about six to about 24 hours. The olefin, or mixture of olefins, used will be straight or branched chain, but preferably straight, having from 26 to 100 carbon atoms, preferably from 30 to 60 carbon atoms. Such olefins can be obtained from any suitable source, but preferably are obtained by polymerizing ethylene in the presence of an aluminum alkyl catalyst, for example, as in U.S. Pat. No. 3,482,000 to Fernald, et al, or by cracking petroleum stocks, and paraffinic materials, such as microcrystalline wax and polyethylene. To separate any unreacted components that may be present the reaction mixture can be subjected to distillation at a temperature of about 150° to about 250° C., preferably about 180° C. to about 220° C., and a pressure of about 0.01 to about 10 pounds per square inch gauge (about 0.069 to about 68.95 kPa), preferably about 0.1 to about 0.5 pounds per square inch gauge (about 0.69 to about 3.45 kPa).

The resulting alkenylsuccinic anhydride can have the following structural formula:

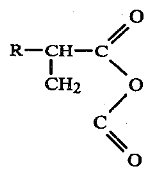

wherein R is an alkenyl group, straight or branched chain, but preferably straight, having from 26 to 100 carbon atoms, preferably from 30 to 60 carbon atoms.

When the alkenylsuccinic anhydride is admixed with water to form the emulsion, it is immediately converted to the corresponding acid. The alkenylsuccinic acids or corresponding anhydrides utilized in the preparation of the emulsions of the present invention are substantially pure. The expression "substantially pure" as used herein means that the alkenylsuccinic material is greater than about 95 weight percent pure, i.e., it contains less than about five weight percent, generally between about two and about four weight percent of an impurity. Such impurity may be unreacted olefin resulting from the preparation of the precursor alkenylsuccinic anhydride as previously described, for example, or other normally water-insoluble material.

As previously indicated, the mixture of alkenylsuccinic acid and water is heated to a temperature above about 63° C., preferably in the range of between about 65° and about 150° C. As will be hereinafter demonstrated, it is essential to the successful formation of a stable emulsion that the mixture of alkenylsuccinic acid and water be heated to a temperature above about 63° C. Otherwise, the resulting emulsion will not be stable and the alkenylsuccinic acid will separate from the water.

The admixture of alkenylsuccinic acid and water are heated to a temperature above about 63° C. and blended for at least about two minutes, preferably between about 10 and 120 minutes. The heating step may be conducted under any suitable pressure including ambient pressure conditions. However, elevated pressures can be utilized, for example, as high as 100 pounds per square inch gauge (689.5 kPa), or even higher, if elevated temperatures are utilized, in order to maintain the water in the system.

After the mixture is heated for the desired time the resulting mixture is cooled to a temperature below about 40° C., preferably to a temperature in the range of between about 10° and about 30° C. The cooled mixture is then vigorously stirred, while maintaining a temperature below about 50° C., preferably in the range of between about 10° and about 30° C., for at least about two minutes, preferably between about five and about 60 minutes.

The amount of water used relative to the alkenylsuccinic acid can vary over a wide range; however, a suitable range of alkenylsuccinic acid to water on a weight basis is between about ¼ to about 10/1, preferably between about 1/1 and about 5/1.

The degree of agitation should be sufficient to provide a stable emulsion. The term "stable emulsion" as used herein means that no appreciable separation of water and alkenylsuccinic acid occurs within a period of at least 10 days. The average particle diameter of the emulsion particles of the substantially pure alkenylsuccinic acid of the present invention are, for example, between about two and about 30 microns, preferably between about three and about 10 microns, with an average particle diameter of between about four and about nine microns being especially preferred.

If desired, excess water can be removed from the emulsion by any suitable means, for example, by mechanical filtration. The resulting emulsion can contain alkenylsuccinic acid and water in a weight ratio of alkenylsuccinic acid to water in the range of between about 90/10 to about 20/80, preferably between about 50/50 and about 20/75.

The following examples illustrate the present invention and are not intended to limit the invention, but rather, are presented merely for purposes of illustration. In each of the examples, an alkenylsuccinic anhydride was used which was prepared by the following procedure. An alpha-olefin fraction was obtained from the product resulting from the telomerization of ethylene in the presence of triethyl aluminum at a temperature of about 200° C. and a pressure of about 3400 pounds per square inch gauge (about 24,443 kPa) over a period of 30–60 minutes and is further defined below in Table 1.

TABLE 1

| Isomer Distribution | Percent By Weight |
|---|---|
| Vinyl | 70.9 |
| Vinylidene | 20.6 |
| cis | 2.1 |
| trans | 4.3 |
| saturates | 2.0 |
| Iodine Number | 47.3 |
| Average Molecular Weight | 529 (corresponds to 37.8 carbon atoms per molecule) |
| Penetration, ASTM D156 | 12 (25° C.) 28 (38° C.) |
| Color, Saybolt, ASTM D156 | +16 (white) |
| Melting Range, °C. | 55–75 |

A mixture of 397 grams of the specific alphaolefin fraction defined above and 83.3 grams of maleic anhydride were stirred and heated at a temperature of about 193° to about 200° C. and ambient pressure in a nitrogen atmosphere for 16 hours. The pressure of the reaction mixture was then reduced to about five to 10 millimeters of mercury and distilled to recover the unreacted maleic anhydride, which amounted to 16.6 grams.

The remaining mixture constituted the alkenylsuccinic anhydride hereinafter used in the examples. The unreacted olefin present in the recovered alkenylsuccinic anhydride amounted to about four weight percent, and when the alkenylsuccinic anhydride was used, it was converted to the corresponding alkenylsuccinic acid upon contact with water. Thus, the expression "alkenylsuccinic acid" as used herein includes the corresponding anhydride.

EXAMPLE I

Fifty grams of alkenylsuccinic acid in granular form were added to 600 milliliters of boiling water and the mixture was maintained at a rolling boil (100° C.) for one-half hour. The resulting solution was cooled to room temperature (26° C.), mixed at high speed in a Waring blender for about five minutes, with the temperature reaching 27° C. Upon cooling to room temperature, the resulting mixture was filtered to remove water using a coarse glass filter. The resulting stable emulsion in the form of an alkenylsuccinic acid-in-water emulsion amounted to 202.8 grams, of which 24.65 weight percent was alkenylsuccinic acid and 73.35 weight percent was water.

EXAMPLE II

One hundred forty-five milliliters of cold water (26° C.) and 50 grams of granular alkenylsuccinic acid were placed in a Waring blender and mixed for about 16 minutes until the temperature reached 70° C. The mixture was at a temperature above 62° C. for about three minutes. The mixture was then cooled to room temperature and subjected to brisk agitation in a Waring blender for about five minutes, during which time the temperature of the mixture reached 30° C. The resulting stable emulsion amounted to 195 grams, of which 25.64 weight percent was alkenylsuccinic acid and 74.36 weight percent was water.

EXAMPLE III

The procedure of Example II was repeated, except that the initial mixing temperature was 65° C. instead of 75° C. The resulting stable emulsion amounted to 195 grams of which 25.64 weight percent was alkenylsuccinic acid and 74.36 weight percent was water.

The following example demonstrates the criticality of the initial heating temperature.

EXAMPLE IV

Fifty grams of granular alkenylsuccinic acid and 145 milliliters of cold water were placed in a Waring blender and mixed for about 13 minutes until the temperature reached 60° C. The mixture was cooled to room temperature and then blended for 11 minutes in a Waring blender until its temperature reached 50° C., cooled to room temperature and then blended again for five minutes until its temperature reached 30° C.

Upon cooling to room temperature there was an immediate separation of water from alkenylsuccinic acid.

EXAMPLE V

Into 1000 milliliters of boiling water there was added 125 grams of granular alkenylsuccinic anhydride and the mixture was stirred for 30 minutes, cooled to room temperature with stirring. The resulting mixture was passed through a coarse glass filter to remove free water, air dried at room temperature to weight constancy and then ground to a powder below 20 mesh.

Into a Waring blender there was added 145 grams of cold water and 50 grams of the acid mixture obtained above and the mixture was blended for four minutes until a temperature of 29° C. was reached. Separation of water from acid occurred. Blending was resumed over a period of 10 minutes until a temperature of 47° C. was reached, and the mixture was then cooled to room temperature. The mixture was again blended for four minutes until a temperature of 30° C. was reached. The resulting emulsion immediately separated upon standing.

EXAMPLE VI

Into a Waring blender there was placed 145 grams of cold water and 50 grams of the acid mixture initially prepared in Example V. The mixture was blended for 12 minutes until a temperature of 55° C. was reached and then cooled to room temperature. The mixture was again blended for three minutes until a temperature of 28° C. was reached and separation of alkenylsuccinic acid from water occurred within one hour. Blending was resumed to a temperature of 65° C. over a period of 15 minutes and the mixture was cooled to room temperature. The mixture was again blended for three minutes until a temperature of 28° C. was reached and the emulsion formed was found to be stable.

The following example demonstrates that the process of the present invention is not necessarily applicable to other high molecular weight acids.

EXAMPLE VII

Fifty grams of stearic acid were added to 300 grams of distilled water in a beaker and the mixture was heated to boiling on a hot plate for a period of one-half hour. Next, the mixture was cooled to room temperature and stirred in a Waring blender for about four minutes.

The mixture began to separate as soon as the blender was turned off, thereby indicating that a stable emulsion had not formed.

Obviously, many modifications and variations of the invention, as hereinabove set forth, can be made without departing from the spirit and scope thereof.

We claim:

1. A process for preparing an alkenylsuccinic acid-in-water emulsion which comprises (a) heating a mixture of water and alkenylsuccinic acid, said alkenylsuccinic acid being greater than about 95 weight percent pure and having the formula

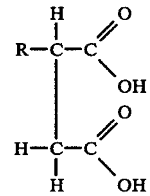

wherein R is an alkyl group having between about 26 and about 100 carbon atoms, at a temperature of between about 63° to about 150° C. for at least about 2 minutes, (b) cooling the resultant mixture to a temperature in the range of between about 10° to below about 40° C., (c) vigorously stirring the cooled mixture while maintaining the temperature in the range of from about 10° to below about 50° C. for at least about 2 minutes thereby forming a stable emulsion wherein the average particle diameter of the emulsion particles is between about 2 and about 30 microns.

2. The process of claim 1 wherein said process is conducted in the absence of an emulsifying agent.

3. The process of claim 1 wherein said mixture is heated to a temperature in the range of between about 65° and about 150° C. for a period of between about 10 and about 120 minutes.

4. The process of claim 1 wherein the heated mixture is cooled to a temperature in the range of between about 10° and about 30° C.

5. The process of claim 1 wherein said emulsion comprises alkenylsuccinic acid particles having an average particle diameter of between about three and about 10 microns.

6. The process of claim 1 wherein said emulsion is filtered to remove excess water.

7. The process of claim 1 wherein said alkenylsuccinic acid is between about 96 and about 98 weight percent pure.

8. The process of claim 1 wherein said mixture is heated to a temperature in the range of between about 65° and about 150° C.

9. The process of claim 1 wherein said mixture is heated for a period of between about 10 and about 120 minutes.

10. The process of claim 1 wherein said emulsion particle size is between about 3 and about 10 microns.

11. An alkenylsuccinic acid-in-water emulsion prepared in accordance with claim 1 wherein said alkenylsuccinic acid is greater than 95 weightpercent pure.

12. A stable emulsion comprising emulsion particles of alkenylsuccinic acid in water, said alkenylsuccinic acid being greater than 95 weight percent pure and having the formula

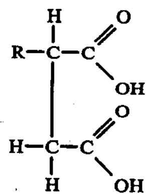

wherein R is an alkyl group having between about 26 and about 100 carbon atoms, said emulsion particles having an average particle diameter of between about 2 and about 30 microns.

13. The emulsion of claim 12 wherein said emulsion contains no emulsifying agent for said alkenylsuccinic acid.

14. The emulsion of claim 12 wherein said emulsion particles have an average particle diameter of between about 3 and about 10 microns.

15. The emulsion of claim 12 wherein said emulsion comprises water, alkenylsuccinic acid, and between about two and about four weight percent unreacted olefin based upon the total weight of the alkenylsuccinic acid and unreacted olefin.

* * * * *